United States Patent [19]

Kawamoto et al.

[11] Patent Number: 5,424,306
[45] Date of Patent: Jun. 13, 1995

[54] CRYSTALLINE CARBAPENEM DERIVATIVE

[75] Inventors: Isao Kawamoto; Masao Miyauchi; Roruro Endo, all of Tokyo, Japan

[73] Assignee: Sankyo Company, Limited, Tokyo, Japan

[21] Appl. No.: 151,517

[22] Filed: Nov. 12, 1993

[30] Foreign Application Priority Data

Nov. 17, 1992 [JP] Japan .................. 4-306884
Jul. 9, 1993 [JP] Japan .................. 5-170267

[51] Int. Cl.$^6$ .............. A01N 43/00; A61K 31/395; C07D 487/04
[52] U.S. Cl. .................. 514/210; 540/350
[58] Field of Search .................. 514/210; 540/350

[56] References Cited

U.S. PATENT DOCUMENTS 5,104,867  4/1992  Kawamoto et al. .......... 514/210
5,242,914  9/1993  Kawamoto et al. .......... 514/210

FOREIGN PATENT DOCUMENTS 0337637  10/1989  European Pat. Off. .
0462521  12/1991  European Pat. Off. .

OTHER PUBLICATIONS

Ritschel, Applied Biopharmacy, 1988, Chapter 19.

*Primary Examiner*—Howard T. Mars
*Assistant Examiner*—Rebecca Cook
*Attorney, Agent, or Firm*—Frishauf, Holtz, Goodman & Woodward

[57] ABSTRACT

A storage stable form of the pivaloyloxymethyl ester of the carbapenem derivative known as (1R, 5S, 6S)-2-[(4R)-2-oxo-4-pyrrolidinylthio]-6-[(1R)-1-hydroxyethyl]-1-methyl-1-carbapen-2-em-3-carboxylic acid in crystalline form.

3 Claims, 1 Drawing Sheet

CRYSTALLINE CARBAPENEM DERIVATIVE

BACKGROUND TO THE INVENTION

The present invention relates to a novel composition of matter which is a specific crystalline form of the pivaloyloxymethyl ester of the carbapenem derivative known as (1R,5S,6S)-2-[(4R)-2-oxo-4-pyrrolidinylthio]-6-[(1R)-1-hydroxyethyl]-1-methyl -1-carbapen-2-em-3-carboxylic acid.

The compound has the formula:

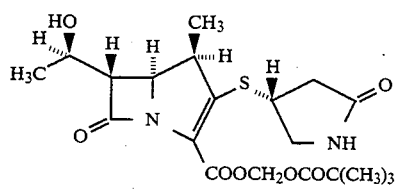

Carbapenem derivatives of this type have good activity as antibiotics and have potential as orally administrable pharmaceutical preparations.

U.S. Pat. No. 5,104,867 and European Patent Publication No. 337 637 disclose (in Example 39) the preparation of a carbapenem derivative which is related to the compound of formula (I) above. By following the prior art procedure of these patents, the carbapenem derivative has previously only been made in the form of an amorphous powder. However, our investigations have shown that the compound of formula (I) which is obtained as an amorphous powder, when prepared according to the methods described in the prior art, is difficult to formulate as an oral pharmaceutical preparation, as well as being slightly unstable, particularly after storage for long periods and is, therefore, of limited practical use as a drug.

We have now surprisingly found that a previously unrealised crystalline form of this compound shows a remarkable and altogether unexpected stability, which makes this carbapenem derivative much easier to handle and formulate and therefore of much greater value as a pharmaceutical.

BRIEF SUMMARY OF THE INVENTION

It is therefore an object of the present invention to provide a compound of formula (I) in crystalline form, preferably in such a form that it is stable and easy to handle and formulate.

It is a further object of the invention to provide a compound of formula (I) in the form of crystals, which compounds have utilisable anti-bacterial activity.

Other objects and advantages of the present invention will become apparent as the description proceeds.

Thus, the present invention provides a crystalline form of pivaloyloxymethyl (1R,5S,6S)-2-[(4R)-2-oxo-4-pyrrolidinylthio]-6-[(1R)-1-hydroxyethyl]-1-methyl-1-carbapen-2-em-3-carboxylate, having the formula (I):

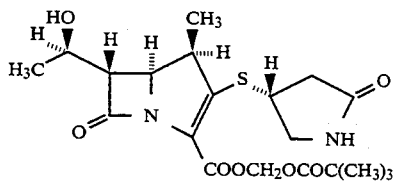

The invention also provides a pharmaceutical composition comprising an antibiotic in admixture with a pharmaceutically acceptable carrier or diluent, wherein the antibiotic is the compound of formula (I) in crystalline form, as hereinabove defined.

The invention further provides a method for the treatment or prophylaxis of bacterial infections in a mammal, e.g. a human being, which comprises administering an effective amount of an antibiotic to said mammal, wherein said antibiotic is the compound of formula (I) in crystalline form as hereinabove defined.

The invention still further provides a process for the preparation of the crystalline form of the compound of formula (I) hereinabove defined, which is described in more detail hereinafter.

Figure 1:
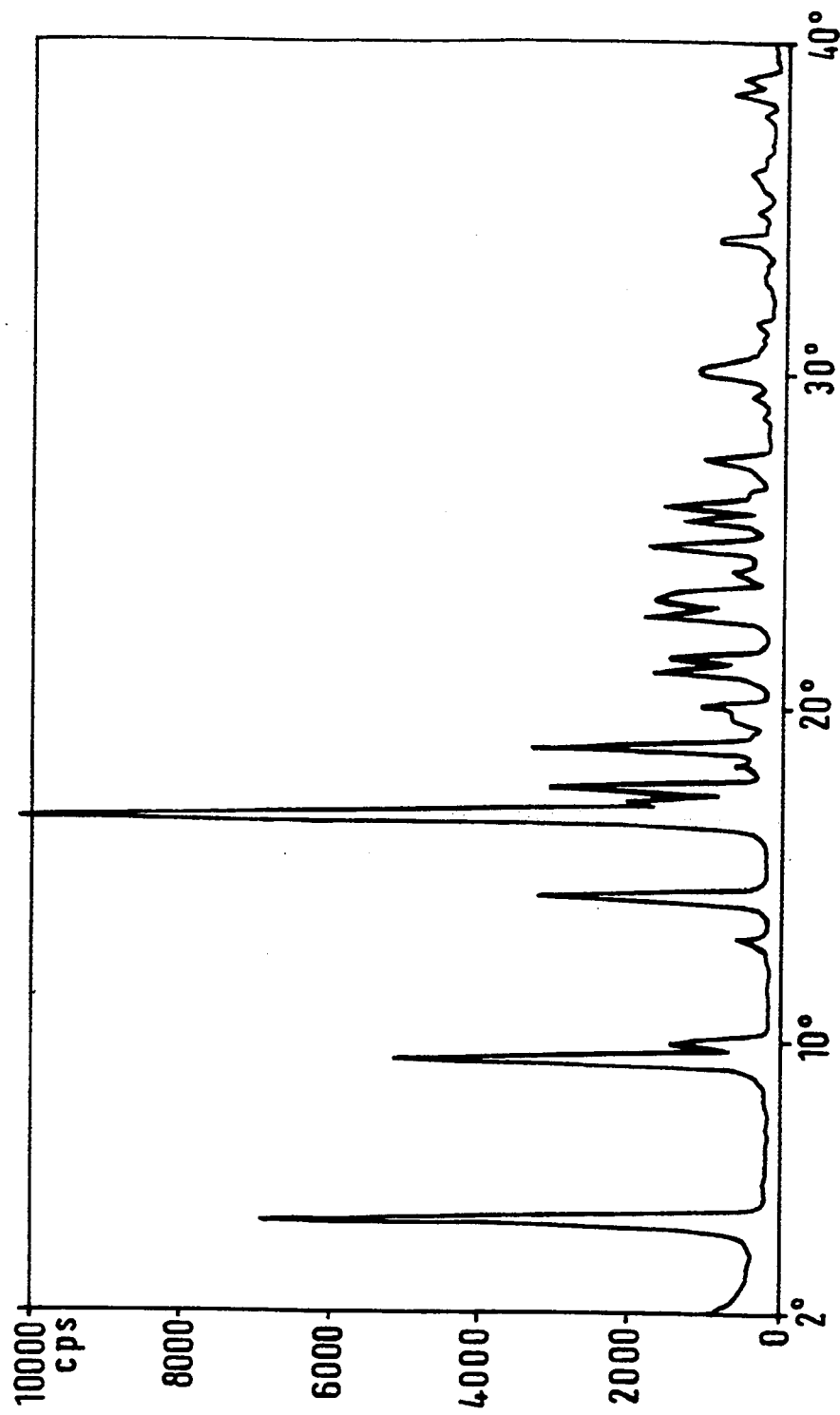
FIG. 1 shows the X-ray diffraction pattern of the crystals of the present invention, by the powder method using the copper $K_\alpha$-ray, $\lambda = 1.54$ Å.

In the drawing, the vertical axis is the diffraction strength in counts per second [cps] and the horizontal axis indicates the value at the diffraction angle $2\theta$.

DETAILED DESCRIPTION OF THE INVENTION

The crystalline form of the compound of formula (I), above, may be characterised by various physical parameters, including the melting point of the crystals and the pattern formed by X-ray diffraction. The preferred crystals of the present invention typically have a melting point of 189° C. These crystals also typically have main peaks at interplanar spacings of 18.41, 9.21, 6.24, 5.28, 5.04 and 4.72 Å determined by X-ray diffraction by the powder method using the copper $K_\alpha$-ray, $\lambda = 1.54$ Å.

The crystalline form of the compound of formula (I) may be prepared by the addition of a solvent to the pivaloyloxymethyl ester of (1R,5S,6S)-2-[(4R)-2-oxo-4-pyrrolidinylthio]-6-[(1R)-1-hydroxyethyl]-1-methyl-1-carbapen-2-em-3-carboxylic acid, followed by active or passive removal of the solvent and washing, drying and isolation of the resulting crystals.

More specifically, the crystals may be prepared by the following steps:

1. Reaction of pivaloyloxymethyl iodide with the sodium salt of (1R,5S,6S)-2-[(4R)-2-oxo-4-pyrrolidinylthio]-6-[(1R)-1-hydroxyethyl]-1-methyl-1-carbapen-2-em-3-carboxylic acid, followed by dilution of the mixture with ethyl acetate. The diluted mixture may then be washed with water and concentrated, for example by evaporation under reduced pressure.

2(a) The residue thus obtained may then be dissolved in a strong solvent. Examples of solvents which are suitable for use in this step include: halogenated hydrocarbons, especially halogenated aliphatic hydrocarbons, such as methylene chloride, 1,2-dichloroethane or chloroform, preferably methylene chloride; dialkyl sulfoxides, such as dimethyl sulfoxide; amides, such as N,N-dimethylformamide and N,N-dimethylacetamide; ketones, such as acetone or 2-butanone, preferably acetone; and alcohols, such as methanol. A weaker solvent or a non-solvent is then suitably added to the solution. Examples of weaker solvents and non-solvents which may be used in this step include: alcohols, such as ethanol; ethers, such as diethyl ether, tetrahydrofuran or dioxane, preferably diethyl ether; esters, such as ethyl acetate; cyclic and aromatic hydrocarbons, such as cyclohexane, toluene or benzene, preferably cyclohexane or toluene; and water. Crystals may then be formed after leaving the mixture to stand and allowing the solvent to evaporate naturally, or by causing at least partial evaporation of the solvent under reduced pressure and then allowing the mixture to stand for further evaporation.

2(b) Alternatively, the residue obtained by the concentration step outlined in Step 1, above, may be dissolved in a mixture of solvents or in a mixture of a solvent and a weak or non-solvent, preferably in a mixture of a strong solvent and a weak or non-solvent, for example in a mixture of methylene chloride and ethanol. The amount of the solvent and weak or non-solvent used in this step and the ratio between the solvent and weak or non-solvent is not critical to the present invention, so long as the solvent and weak or non-solvent are present at an amount and a ratio sufficient to allow crystallization to take place. We have found that a ratio of methylene chloride to ethanol of from about 4:1 to about 1:4 by volume, preferably of from about 1:1 to about 1:4 by volume, is sufficient for this purpose. However a ratio of from about 1:1 to 1:2 by volume is most preferably used. Crystals may then be formed after leaving the mixture to stand and allowing the solvent to evaporate naturally, or by causing at least partial evaporation of the solvent under reduced pressure and then allowing the mixture to stand for further evaporation.

The crystals obtained by the steps outlined above may then be washed, dried and isolated using standard procedures. Typically, the crystals are washed with, for example, ethanol and dried under reduced pressure and at a temperature of from about 20° C. to 25° C.

The crystals of the present invention obtained by following the steps outlined above, melt at about 189° C. and have main peaks at interplanar spacings of 18.41, 9.21, 6.24, 5.28, 5.04 and 4.72 Å, as determined by X-ray diffraction by the powder method using the copper $K_\alpha$-ray, $\lambda = 1.54$ Å.

The crystals of the present invention have excellent antibacterial activity against a broad spectrum of gram-positive, gram-negative and cephalosporinase-producing bacteria, of an order comparable with that of the compound of formula-(I) in powder form, particularly when administered orally.

After incubation at 37° C. for one hour in horse serum, the antibacterial activity of the crystals of the invention was assessed by the agar plate dilution method. In this manner, the crystals of the invention have been shown to be active against a wide range of pathogenic micro-organisms, including gram-positive bacteria, such as *Staphylococcus aureus* and *Enterococcus faecalis*, as well as gram-negative bacteria, such as *Escherichia coli*, *Shigella* species, *Klebsiella pneumoniae*, *Proteus* species, *Serratia* species, *Enterobacter* species and *Pseudomonas aeruginosa*, as well as anaerobic bacteria, such as *Bacteroides fragilis*, and are thus very useful for the treatment of diseases caused by such micro-organisms in humans and non-human animals.

After oral administration of the crystals of the present invention to mice thoroughly infected throughout the body with either *Staphylococcus aureus* or *Escherichia coli*, the resulting therapeutic effects were excellent.

Furthermore, large amounts of the acid form of the compound of formula (I) were recovered from the urine of the mice, after oral administration of the compound of formula (I) in crystalline form.

The crystals of the compound of formula (I) also have low toxicity, this toxicity being less than that of the compound of formula (I) in amorphous form probably because of the freedom of the present crystals from decomposition products. The crystals of the compound of formula (I) are thus of potentially great value as therapeutic agents in the treatment of bacterial infections.

Furthermore, the crystals of the present invention do not decompose after standing for several weeks at a temperature of 60° C., thus showing that the crystalline form has a much higher stability than the amorphous powdered form, as is illustrated hereinafter in the following Experiment.

The crystals of the invention may be administered orally for the treatment of diseases in humans and other animals caused by pathogenic micro-organisms. The crystals may be formulated into any conventional form for administration. For example, for oral administration, the crystals may be mixed with suitable pharmaceutically acceptable excipients including, for example: starch; a sugar, such as lactose or sucrose, an alkali metal carbonate, such as calcium carbonate, potassium carbonate or magnesium carbonate, preferably calcium carbonate; an alkali metal phosphate, such as calcium phosphate, magnesium phosphate or potassium phosphate, preferably calcium phosphate; an ether, such as polyethylene glycol; a binder, such as gum arabic, carboxymethylcellulose, hydroxpropylcellulose, gelatin or polyvinyl pyrrolidone; a lubricant, such as magnesium stearate, talc, sodium lauryl sulfate or polyethlene glycol; a disintegrating agent, such as alginic acid, alginic acid salts, or a calcium salt of carboxymethylcellulose; colorants; flavors; and sweetening agents. Suitable formulations for oral administration of the crystals of the present invention include tablets, granules, capsules, powders and syrups.

The dose of the crystals of the invention will vary, depending on the nature of the disease to be treated, the symptoms, age, body weight and condition of the patient, as well as upon the form and times of administration. However, in general the adult daily dose is expected to be from 50 mg to 2 g of the crystals, which may be administered in a single dose or twice to four times daily.

EXPERIMENT

Stability of Compound of Formula (I) in Crystalline Form

The crystals obtained by following Example 1, hereinafter, and the amorphous powder form of the compound of formula (I), prepared by following substantially the same procedure as is described in Example 39 of European Patent Publication No. 337 637 (or Example 16 of Japanese Patent Publication No. Hei 2-49783) were stored in a silica gel dessicator at a temperature of 60° C. The stability of the two compounds after 7 days and at the end of 28 days in these conditions was tested by determining the amount of the compound remaining. Testing was performed by high performance liquid chromatography (HPLC), under the following conditions:

Column: Inertsil ODS-2 (4.6 mm diameter × 150 mm)

Mobile phase: 20 mM 3-(N-morpholino)propanesulfonic acid buffer (pH 7): CH$_3$CN=70:30 by volume Detection: Ultraviolet absorption at 322 nm

TABLE 1

| Compound | Temperature | Test Period (Days) 7 | 28 |
|---|---|---|---|
| Crystalline powder (crystals obtained in Example 1) | 60° C. | 99.2% | 98.1% |
| Non-crystalline powder | 60° C. | 91.6% | 68.2% |

The preparation of the crystals of the present invention is further illustrated in the following Example and Preparations. In the following Examples and Preparations, Nuclear Magnetic Resonance spectrum measurements were made using tetramethylsilane as an internal or external standard, unless otherwise indicated.

EXAMPLE 1

4.76 g of the sodium salt of (1R,5S,6S)-2-[(4R)-2-oxo-4-pyrrolidinylthio]-6-[(1R)-1-hydroxyethyl]-1-methyl-1-carbapen-2-em-3-carboxylic acid [prepared as described in Preparation 6] were dissolved in 35 ml of N,N-dimethylacetamide. 3.60 g of pivaloyloxymethyl iodide were then added to the resulting solution, whilst ice-cooling, and the mixture was stirred for 30 minutes. At the end of this time, the mixture was diluted with ethyl acetate, after which the mixture was washed with water and a saturated aqueous solution of sodium chloride. The ethyl acetate layer was then dehydrated using anhydrous sodium sulfate, and then concentrated by evaporation under reduced pressure. The resulting residue in the form of an amorphous powder, 4.54 g, was then dissolved in a 1:1 by volume mixture of ethanol and methylene chloride, after which crystals were formed by evaporation of the methylene chloride under reduced pressure. The resulting crystals were collected after removal of the remaining ethanol by filtration and, after drying, 3.68 g of colorless crystals were obtained; melting at 189° C.

Infrared Absorption Spectrum (KBr) $\nu_{max}$ cm$^{-1}$:
3336, 1764, 1751, 1717, 1691, 1542, 1347, 1213, 1160, 1114, 995.

Ultraviolet Absorption Spectrum (CH$_3$CN) λ max nm: 324

Nuclear Magnetic Resonance Spectrum: (400 MHz, hexadeuterated dimethyl sulfoxide, internal standard: tetramethylsilane) δ ppm:
1.10–1.18 (15H, multiplet);
2.11 (1H, doublet of doublets, J=17.0 and 4.3 Hz);
2.78 (1H, doublet of doublets, J=17.0 and 7.7 Hz);
3.09 (1H, doublet of doublets, J=10.9 and 3.9 Hz);
3.25 (1H, doublet of doublets, J=6.2 and 2.5 Hz);
3.44–3.48 (1H, multiplet);
3.71 (1H, doublet of doublets, J=10.9 and 7.6 Hz);
3.94–4.00 (1H, multiplet);
4.04–4.09 (1H, multiplet);
4.23 (1H, doublet of doublets, J=9.5 and 2.5 Hz);
5.08 (1H, doublet, J=5.1 Hz);
5.73 (1H, doublet, J=5.9 Hz);
5.88 (1H, doublet, J=5.9 Hz);
7.84 (1H, singlet).

The X-ray diffraction pattern of the crystals obtained by use of the powder method using the copper K$_\alpha$-ray, λ=1.54 Å, is shown in FIG. 1.

PREPARATION 1

(4R)-4-Acetylthio-2-oxopyrrolidine 1-(1) (4S)-4-Methanesulfonyloxy-2-oxopyrrolidine 1.90 g of (4S)-4-hydroxy-2-oxopyrrolidine were dissolved in 100 ml of pyridine, after which 2.26 g of methanesulfonyl chloride were added dropwise to the solution, whilst stirring and ice-cooling. The resulting mixture was then stirred at room temperature for 1.5 hours, after which the reaction mixture was concentrated by evaporation under reduced pressure. 9 ml of a saturated aqueous solution of sodium hydrogencarbonate were then added to the mixture, and the mixture was again concentrated to dryness by evaporation under reduced pressure. A 1:1 by volume mixture of ethyl acetate and methanol was then added to the resulting residue, after which the insoluble portion was removed by filtration and the soluble portion was concentrated by evaporation under reduced pressure. The residue obtained from the soluble portion was subjected to column chromatography (Merck 9385, 150 ml) through silica gel using a gradient elution method, with mixtures of ethyl acetate and methanol ranging from 9:1 to 4:1 by volume as the eluent. The fractions containing the compound of the invention were combined and concentrated by evaporation under reduced pressure, and the desired compound was recrystallized from a mixture of ethyl acetate and methanol to produce 2.44 g of the title compound as crystals, melting between 137.5° and 139° C.

Optical rotation [α]$_D^{24}$ −35.5° (C=1.09, MeOH);
Infrared Absorption Spectrum, (KBr) $\nu_{max}$ cm$^{-1}$:
1719, 1697, 1659, 1305, 1177, 1171, 1159, 963.

Nuclear Magnetic Resonance Spectrum: (400 MHz, hexadeuterated dimethyl sulfoxide) δ ppm:
2.28 (1H, doublet of doublets, J=17.6, 1.8 Hz);
2.71 (1H, doublet of doublets, J=17.6, 6.3 Hz);
3.24 (3H, singlet);
3.37 (1H, doublet, J=11.9 Hz);
3.66 (1H, doublet of doublets, J=11.9, 5.3 Hz);
5.31–5.34 (1H, multiplet);
7,85 (1H, broad singlet).

1-(2) (4R)-4-Acetylthio-2-oxopyrrolidine 896 mg of the compound obtained in step (1), above, were dissolved in 90 ml of anhydrous acetonitrile, and 857 mg of potassium thioacetate were then added to the solution. The solution was then heated to reflux in an 85° C. oil bath and maintained at that temperature for 2 hours. At the end of this time, insoluble matter was removed from the reaction mixture by filtration, and the filtrate was concentrated by evaporation under reduced pressure. Ethyl acetate was then added to the residue and any insoluble matter was again removed by filtration. The soluble portion was then subjected to column chromatography through silica gel using a gradient elution method, with ethyl acetate alone or mixtures of ethyl acetate and methanol, ranging from 98:2 to 96:4 to 94:6 by volume, as the eluent. The desired fractions were combined and concentrated by evaporation under reduced pressure to obtain 593 mg of a crystalline residue. This residue was recrystallized from a mixture of ethyl acetate and cyclohexane to give 455 mg of the title compound as crystals, melting at 59° to 60° C.

Optical rotation $[\alpha]_D^{25} +47.3°$ (C=1.33, MeOH).
Infrared Absorption Spectrum (KBr) $\nu_{max}$ cm$^{-1}$: 1689, 1125.
Nuclear Magnetic Resonance Spectrum: (400 MHz, CDCl$_3$) δ ppm:
 2.30 (1H, doublet of doublets, J=17.4, 6.0 Hz);
 2.35 (3H, singlet);
 2.80 (1H, doublet of doublets, J=17.4, 9.1 Hz);
 3.31 (1H, doublet of doublets, J=10.2, 5.1 Hz);
 3.89 (1H, doublet of doublets, J=10.2, 7.2 Hz);
 4.15–4.23 (1H, multiplet);
 7.27 (1H, broad singlet).

PREPARATION 2

(4R)-4-Acetylthio-2-oxopyrrolidine 380 mg of (4S)-4-hydroxy-2-oxopyrrolidine were suspended in 21 ml of anhydrous tetrahydrofuran, and 1.18 g of triphenylphosphine were added to the suspension at room temperature. 783 mg of diethyl azodicarboxylate were then added dropwise to the solution, whilst maintaining a temperature of −30° C. The mixture was then gradually heated to 4° C., after which the mixture was stirred at the same temperature for 30 minutes to produce a homogeneous mixture. At the end of this time, the reaction mixture was cooled to −20° C., and then 320 μl of thioacetic acid were added dropwise to the cooled mixture. The resulting mixture was gradually heated to a temperature equivalent to ice-cooling; and the mixture was stirred for 1.5 hours at that temperature. At the end of this time, the reaction mixture was concentrated by evaporation under reduced pressure, and then subjected to column chromatography (Merck 9385, 60 ml) through silica gel using a gradient elution method, with mixtures of benzene and acetonitrile ranging from 2:1 and 1:1 by volume as the eluent. The desired fraction was concentrated by evaporation under reduced pressure to give 69 mg of a crystalline residue. This residue was recrystallized from a mixture of ethyl acetate and cyclohexane to give 54 mg of the title compound as crystals.

The melting point, optical rotation, Infrared Absorption Spectrum and Nuclear Magnetic Resonance Spectrum of the compound obtained in this manner were identical with the corresponding values of the compound obtained in Step (2) of Preparation 1, above.

PREPARATION 3

(4R)-4-Acetylthio-2-oxopyrrolidine 3-(1) (4S)-4-[(1S)-10-Camphorsulfonyloxy]-2-oxopyrrolidine 1011 mg 4-hydroxy-2-oxopyrrolidine were dissolved in 50 ml of pyridine, and 2.63 mg of (1S)-10-camphorsulfonic acid chloride were then added to the mixture, whilst ice-cooling. The mixture was then stirred for 10 minutes at that temperature, after which the mixture was stirred at room temperature for 30 minutes. At the end of this time, the reaction mixture was concentrated by evaporation under reduced pressure. The resulting residue was then dissolved in ethyl acetate, after which the mixture was washed with a saturated aqueous solution of sodium chloride. The ethyl acetate layer was then concentrated be evaporation under reduced pressure, and the residue obtained was subjected to column chromatography (Merck 9385, 100 ml) through silica gel using the gradient elution method, with ethyl acetate alone or mixtures of ethyl acetate and methanol, ranging from 95:5 to 9:1 by volume, as the eluent. The desired fraction was concentrated by evaporation under reduced pressure and then dissolved in 50 ml of ethyl acetate. The solution was then left to stand. The crystals which precipitated from this mixture were collected by filtration and then dried to give 262 mg of the title compound, melting at between 114° and 116° C.

Nuclear Magnetic Resonance Spectrum: (270 MHz, CDCl$_3$) δ ppm:
 0.89 (3H, singlet);
 1.10 (3H, singlet);
 1.47 (1H, double doublet of doublets, J=12.5, 9.2, 3.3 Hz);
 1.70 (1H, double doublet of doublets, J=13.8, 9.2, 4.6 Hz);
 1.97 (1H, doublet, J=17.5 Hz);
 2.02–2.17 (2H, multiplet);
 2.35–2.49 (2H, multiplet);
 2.63 (1H, doublet of doublets, J=17.8, 2.6 Hz);
 2.79 (1H, doublet of doublets, J=17.8, 6.6 Hz);
 3.05 (1H, doublet, J=15.0 Hz);
 3.61 (1H, doublet, J=15.0 Hz);
 3.66 (1H, doublet, J=11.9 Hz);
 3.82 (1H, doublet of doublets, J=11.9, 6.0 Hz);
 5.43–5.48 (1H, multiplet);
 6.01 (1H, broad singlet).

3-(2) (4R)-4-Acetylthio-2-oxopyrrolidine 160 mg of the compound obtained in step 1, above, were dissolved in 16 ml of dry acetonitrile, and 90 mg of potassium thioacetate were then added to the resulting solution. The mixture was then heated to reflux in a 90° C. oil bath for 5 hours. At the end of this time, a procedure similar to that described in step (2) of Preparation 1 was followed, to produce 61 mg of the title compound as crystals. The melting point, optical rotation, Infrared Absorption Spectrum and Nuclear Magnetic Resonance Spectrum for the compound obtained in this manner were identical to those values for the compound obtained by following the procedure of Preparation 1.

PREPARATION 4

(4R)-4-Mercapto-2-oxopyrrolidine 375 mg of (4R)-4-acetylthio-2-oxopyrrolidine [prepared as described in any one of Preparations 1 to 3, above] were dissolved in 5 ml of methanol, and 2.35 ml of a 1N solution of sodium methylate in methanol were then added to the resulting mixture, whilst ice-cooling. The mixture was then stirred for 20 minutes at that temperature. At the end of this time, 2.35 ml of a 1N aqueous solution of hydrogen chloride was added to the reaction mixture, after which the mixture was concentrated to dryness by evaporation under reduced pressure. Ethyl acetate was then added to the residue and any insoluble matter was removed by filtration. The soluble portion in ethyl acetate was then concentrated by evaporation under reduced pressure to give 275 mg of the title compound as crystals, melting at between 69.5° and 70° C.

Optical rotation $[\alpha]_D^{24} +36.5°$ (C=1.18, MeOH).
Infrared Absorption Spectrum: (KBr) $\nu_{max}$ cm$^{-1}$: 2539, 1699, 1683.
Nuclear Magnetic Resonance Spectrum: (400 MHz, CDCl$_3$) δ ppm:
 1.96 (1H, doublet, J=7.2 Hz);
 2.32 (1H, doublet of doublets, J=17.2, 6.8 Hz);
 2.80 (1H, doublet of doublets, J=17.2, 8.2 Hz);
 3.32 (1H, doublet of doublets, J=10.2, 5.6 Hz);
 3.62–3.70 (1H, multiplet);

3.81 (1H, doublet of doublets, J=10.2, 7.3 Hz);
7.27 (1H, broad singlet).

PREPARATION 5

4-Nitrobenzyl (1R,5S,6S)-2-[(4R)-2-oxo-4-pyrrolidinylthio]-6-[(1R)-1-hydroxyethyl]-1-methyl-1-carbapen-2-em-3-carboxylate 1000 mg of 4-nitrobenzyl (1R,5S,6S)-2-diphenylphosphonyloxy-6-[(1R)-1-hydroxyethyl]-1-methyl-1-carbapen-2-em-3-carboxylate [prepared as described in Japanese Patent Publication No. Hei 4-330085] were dissolved in 10 ml of acetonitrile. A solution of 200 mg of (4R)-4-mercapto-2-oxopyrrolidine [prepared as described in Preparation 4] in 3 ml acetonitrile and 296 l of diisopropylethylamine was then added to the reaction mixture, whilst ice-cooling. The resulting mixture was then stirred for 1 hour at that temperature, and then left to stand overnight at 4° C. The crystalline compound which precipitated from the reaction mixture during this period was collected by filtration and dried to give 672 mg of the title compound, melting at between 219° and 221° C.

Nuclear Magnetic Resonance Spectrum: (270 MHz, hexadeuterated dimethyl sulfoxide) δ ppm:
1.16 (3H, doublet, J=6.3 Hz);
1.17 (3H, doublet, J=7.3 Hz);
2.13 (1H, doublet of doublets, J=17.1 and 4.4 Hz);
2.79 (1H, doublet of doublets, J=17.1 and 7.8 Hz);
3.10 (1H, doublet of doublets, J=10.8 and 3.4 Hz);
3.16–3.35 (1H, multiplet);
3.40–3.51 (1H, multiplet);
3.70 (1H, doublet of doublets, J=10.7 and 7.3 Hz);
3.95–4.12 (2H, multiplet);
4.25 (1H, doublet of doublets, J=9.3 and 2.5 Hz);
5.07 (1H, doublet, J=5.4 Hz);
5.30, 5.46 (2H, AB, J=14.2 Hz);
7.71 (2H, doublet, J=8.8 Hz);
8.23 (2H, doublet, J=8.8 Hz).

PREPARATION 6

Sodium (1R,5S,6S)-2-[(4R)-2-oxo-4-pyrrolidinylthio 1-6-[(1R)-1-hydroxyethyl]-1-methyl-1-carbapen-2-em-3-carboxylate 390 mg of the compound obtained in Preparation 5, above, were dissolved in a mixture of 19 ml of tetrahydrofuran and 18 ml of a 0.1M aqueous phosphate buffer solution. 300 mg of a 10% w/w palladium-on-carbon catalyst were then added to the reaction mixture, and the mixture was stirred vigorously in an atmosphere of hydrogen for 2.5 hours. At the end of this time, the catalyst was removed from the reaction mixture by filtration, and the filtrate was washed twice with diethyl ether. The aqueous layer was then concentrated by evaporation under reduced pressure, and the resulting residue was subjected to chromatography through a MCI GEL CHP-20P (a trademark for a product of Mitsubishi Kasei Corporation, 75 to 150 μm, 50 ml) developed with water. The desired fraction was then concentrated by evaporation under reduced pressure, after which the residue was freeze-dried to give 225 mg of the title compound as a colorless powder.

Nuclear Magnetic Resonance Spectrum: (270 MHz, deuterated water) δ ppm:
1.02 (3H, doublet, J=7.3 Hz);
1.10 (3H, doublet, J=6.6 Hz);
2.22 (1H, doublet of doublets, J=17.6 and 4.4 Hz);
2.77 (1H, doublet of doublets, J=17.6 and 8.4 Hz);
3 08–3.25 (2H, multiplet);
3.25 (1H, doublet of doublets, J=5.9 and 2.6 Hz);
3.68 (1H, doublet of doublets, J=11.4 and 6.4 Hz);
3.84–3.96 (1H, multiplet);
4.00–4.12 (2H, multiplet).

We claim:

1. Pivaloyloxymethyl (1R, 5S, 6S)-2-[(4R)-2-oxo-4-pyrrolidinylthio]-6-[(1R)-1-hydroxyethyl]-1-methyl-1-carbapen-2-em-3-carboxylate, having the formula (I):

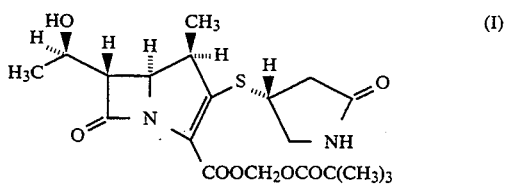

in crystalline form having main peaks at interplanar spacings of 18.41, 9.21, 6.24, 5.28, 5.04 and 4.72 Å determined by X-ray diffraction by the powder method using the copper $K_\alpha$-ray, $\nu=1.54$ Å and having a melting point of 189° C.

2. A pharmaceutical composition comprising an antibacterial effective amount of an antibiotic in admixture with a pharmaceutically acceptable carrier or diluent, wherein the antibiotic is the compound of formula (I) in crystalline form, as defined in claim 1.

3. A method for the treatment or prophylaxis of bacterial infections in a mammal which comprises administering an effective amount of an antibiotic to said mammal, wherein said antibiotic is the compound of formula (I) in crystalline form, as defined in claim 1.

* * * * *